United States Patent [19]

Baker, Jr.

[11] Patent Number: 5,222,494
[45] Date of Patent: Jun. 29, 1993

[54] IMPLANTABLE TISSUE STIMULATOR OUTPUT STABILIZATION SYSTEM
[75] Inventor: Ross G. Baker, Jr., Houston, Tex.
[73] Assignee: Cyberonics, Inc., Webster, Tex.
[21] Appl. No.: 738,801
[22] Filed: Jul. 31, 1991
[51] Int. Cl.⁵ .............................................. A61N 1/08
[52] U.S. Cl. .............................. 128/421; 128/419 PT
[58] Field of Search ............... 128/419 PT, 421, 419 R

[56] References Cited
U.S. PATENT DOCUMENTS
3,746,006  7/1973  Thaler ......................... 128/419 PT
4,738,250  4/1988  Fulkerson et al. .................. 128/421

Primary Examiner—William E. Kamm
Assistant Examiner—Scott M. Getzow
Attorney, Agent, or Firm—Leitner, Greene & Christensen

[57] ABSTRACT

Apparatus is disclosed for stabilizing the value of a parameter of the output pulses of a tissue stimulator, such as the magnitude of the current or the charge delivered in each output pulse to excite the cell membranes of the tissue to be stimulated. The apparatus measures the value of this parameter against target limits, and if either limit is exceeded, adjusts the value of a second parameter of the output pulses, such as voltage level or pulse width, to stabilize the value of the first parameter. The value of the first parameter may be measured by sampling thereof at a rate considerably less than the frequency of the output pulses, and the value of the second parameter then adjusted to bring the value of the first parameter within the target limits. Both current and charge stabilization modes of the pulse generating stimulator for efficient excitation of cell membranes of the selected tissue are described.

32 Claims, 3 Drawing Sheets

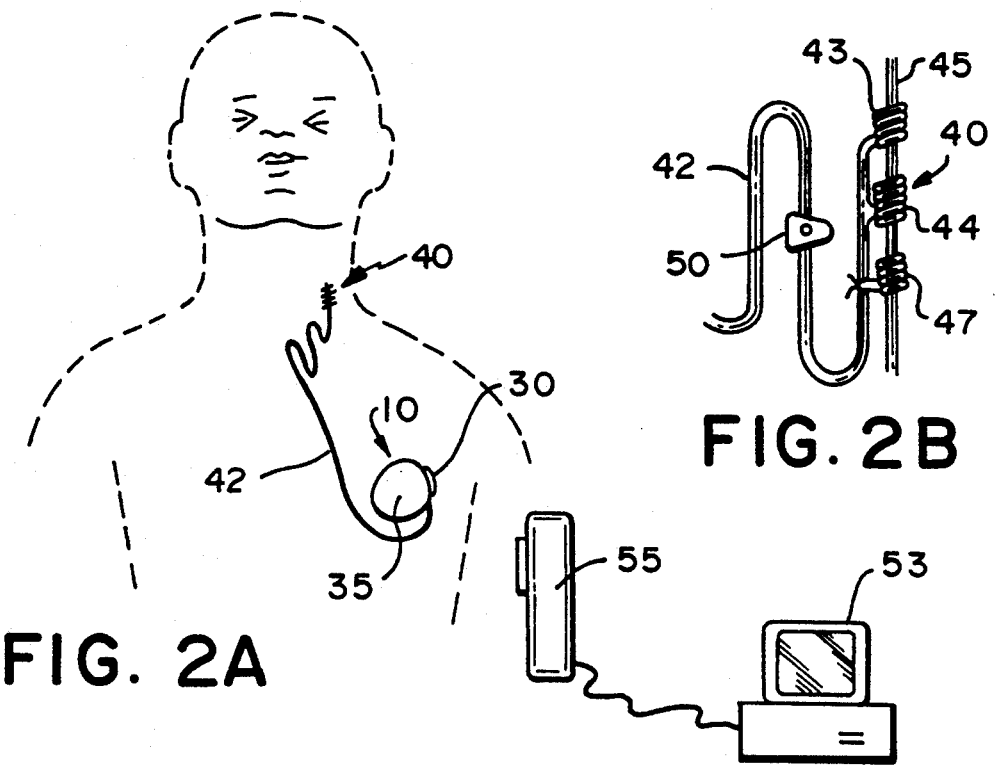
FIG. 2A
FIG. 2B
FIG. 4
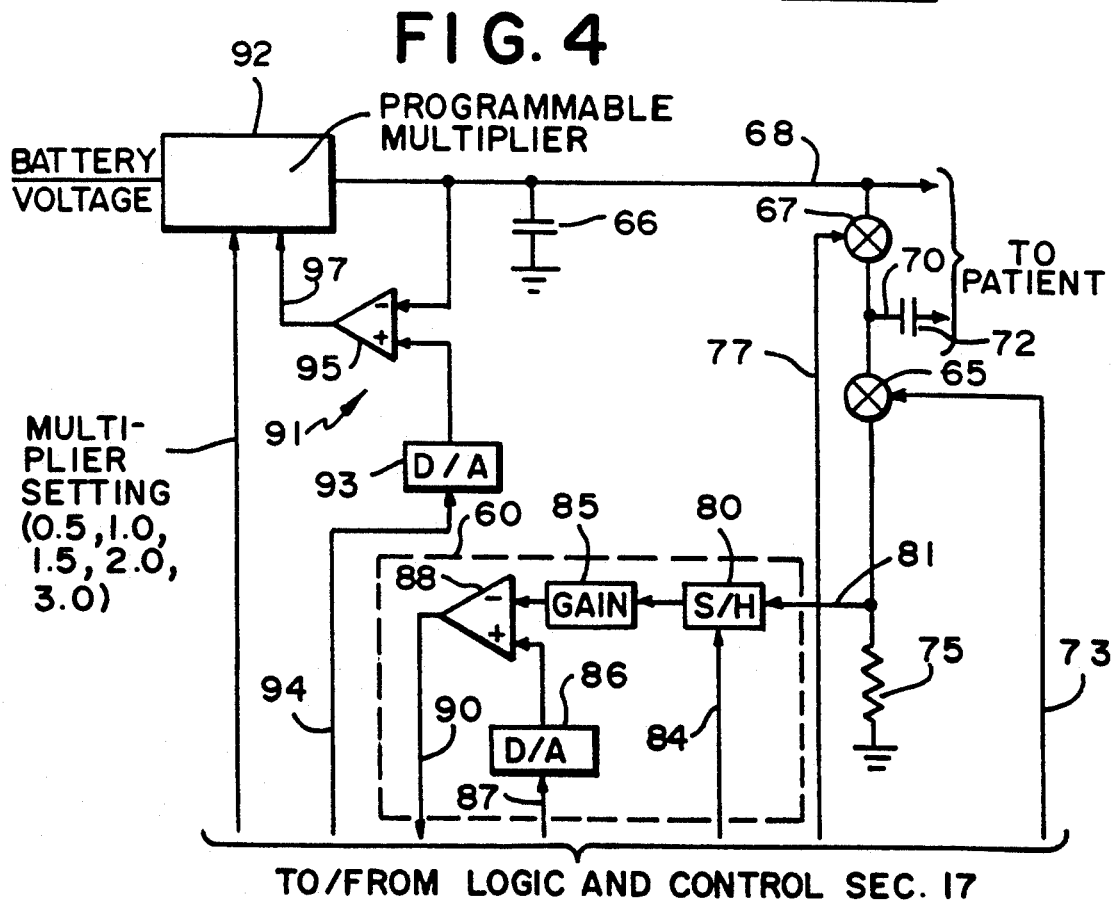

IMPLANTABLE TISSUE STIMULATOR OUTPUT STABILIZATION SYSTEM

BACKGROUND OF THE INVENTION

The present invention relates generally to excitable tissue stimulation, and more particularly to improvements in energy efficiency of implantable neurostimulators utilized in conjunction with one or more electrodes which are surgically implanted on a selected nerve or nerves of the patient to permit electrical stimulation thereof.

Implantable neurostimulators employ one or more batteries as the power source for the device When the power is depleted, it becomes necessary to perform surgical removal and replacement of the device. It is desirable, therefore, to conserve device energy to the extent possible, while supplying stimulation as needed, in order to prolong device lifetime and increase the interval between surgical replacements. Of course, such considerations are important for any implantable medical device, not merely neurostimulating devices Ideally, cardiac and neuromuscular stimulators have output circuits which may characterize them as constant voltage or constant current devices. In practice, however, presently available implantable versions of these devices depart significantly from the constant output ideal models.

The constant current mode of the existing devices has the advantage that changes in system resistance or impedance do not affect the output current of the device. For neurostimulation, this is important because it is the current applied to the nerve which causes excitable fiber depolarization. The constant current mode also tends to limit the possibility of damage to the nerve being stimulated. Nerve damage might occur, for example, from any overstimulation resulting from changes in system impedance that cause current variations.

Despite its advantages, however, constant current stimulation has certain drawbacks A constant output current system generally requires that the supply voltage must be significantly greater than the voltage which is actually delivered to the nerve electrode. This excess voltage is dropped across the constant current regulating circuit and may represent significant energy waste, which, for reasons noted above, results in the need for undesirably frequent replacements of implanted systems. Another problem is the excess energy consumption in the control circuit of the constant current system. This circuit is required to have a sufficiently rapid response time to permit controlling the output current during even very brief output pulses. Therefore, amplifier bias currents must be set relatively high, with consequent energy overhead The control circuit may be designed without an active amplifier, but would then possess the disadvantage of requiring even greater supply voltage overhead.

SUMMARY OF THE INVENTION

The present invention provides an implantable neurostimulator which encompasses two modes of output circuit operation, each of which combines at least some of the advantages of constant current devices with the greater efficiency of constant voltage devices. Specifically, the output circuit of the neurostimulator pulse generator according to the present invention employs either of two operating modes; namely, (i) a current stabilization mode or (ii) a charge stabilization mode.

The neurostimulator generates a desired signal, typically a pulse waveform having preprogrammed parameter values, which is delivered via an electrode array implanted on a nerve or nerves of a patient, to excite the cell membranes in the nerve tissue and thereby modulate the electrical activity of the nerve in the desired manner. In the preferred embodiment of a current stabilization mode system, the neurostimulator pulse generator generates a sequence of output pulses or output pulse bursts according to a predetermined pattern, and a control loop connected to the pulse generator measures the magnitude of the current in the output pulses on a sampled basis, compares the sampled current value to a prescribed target value, and adjusts the voltage of the output pulses to reduce or eliminate any discrepancy between the two to stabilize the output pulse current.

For purposes of sampling, the control loop measurements of pulse current level are taken at a rate considerably less than the frequency at which the output pulses are generated. The adjustment circuit of the control loop also performs at a relatively slow rate which further helps to conserve energy in the nerve stimulation system.

Preferably, the control loop includes a limit circuit for establishing predetermined high and low control limits for the current magnitude of the output pulses, and produces an adjustment of an appropriate parameter of the output pulses to return the output pulse current to a level within those limits whenever one of the limits is exceeded. Alternatively, the measurement circuit means may include means for performing successive approximations of the output current magnitude by measuring one output pulse per burst and completing the approximation after a sequence of the bursts.

In the preferred embodiment of the current stabilization mode system, the measurements are taken by sampling at the trailing edge of the selected output pulses. Alternatively, the sampling may be performed at the midpoint of the selected output pulses.

The charge stabilization mode functions in a similar way, but measures the charge delivered in each sample by integrating the sampled current over a preset time interval, specifically the output pulse duration, and compares that value to a target charge level. Any discrepancy between the two is reduced by adjusting the duration of the output pulses to maintain the charge delivered in the output pulses at a desired level for nerve cell membrane excitation.

Accordingly, it is a broad object of the present invention to provide an implantable excitable tissue stimulating device having reduced energy overhead.

A more specific object of the invention is to provide an improved implantable neurostimulator having an output circuit adapted to generate pulses in either a current stabilized mode or a charge stabilized mode for operating efficiency and conservation of battery power.

Another object of the invention is to provide apparatus and methods for stabilizing the output energy delivered from an implanted electrical device to excitable tissue of a patient to produce desired stimulation of the tissue without significant energy losses, by relatively frequent but not continuous measurement and adjustment of the output energy to a target level.

It is a further object of the preset invention to achieve these and other objects of the invention by means of a stabilization system which performs sampling of the selected parameter of the output pulses of the tissue stimulator, such as a neurostimulator, rather than operating in a continuous measurement and adjustment mode.

BRIEF DESCRIPTION OF THE DRAWINGS

The above and still further objects, features and attendant advantages of the invention will become apparent from a consideration of the following detailed description of the preferred embodiments thereof, taken in conjunction with the accompanying drawings, in which:

FIGS. 2A and 2B are, respectively, a phantom view illustrating the relative positions of the neurostimulator, nerve electrode array (implanted, for example, on the vagus nerve) and associated electrical leads implanted in the patient, and indicating associated external equipment; and a detailed view of the electrode array of FIG. 2A implanted on the selected nerve;

FIG. 4 is a block diagram of the circuitry employed in the neurostimulator of FIG. 1, to implement the preferred embodiment of the current stabilization mode of the invention.

DETAILED DESCRIPTION OF THE PREFERRED EMBODIMENTS AND METHODS

Figure 1:
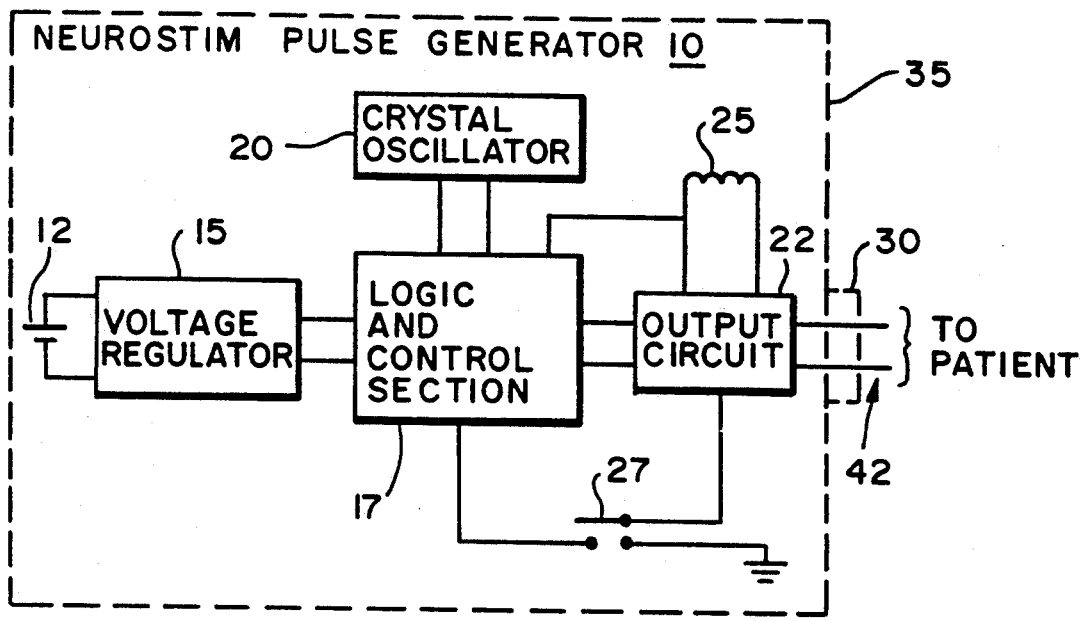
FIG. 1 is a simplified block diagram of a exemplary implantable neurostimulator in which the present invention may be utilized.

According to the present invention, the output circuit of an excitable tissue stimulating implantable pulse generator may employ either of two output stabilization modes, namely (i) current stabilization or (ii) charge stabilization.

The current stabilization mode employs a constant voltage output circuit combined with a circuit including a digital control system, preferably comprising a microprocessor, which, among other things, measures the current in the output pulse waveform. The measurement may be made during each pulse or only during selected pulses of the output pulse sequence. The digital control system uses the measurement information to adjust the output voltage to stabilize the output current at a desired level or within predefined limits. Unlike prior art "constant current" devices, the control loop of tee current stabilization mode consumes relatively little energy, i.e., has low "energy overhead", in part because the measurements need not be made in every pulse cycle, and may be performed at a very slow rate over multiple output pulses. Adjustment of the energy in the output pulse waveform based on these measurements may also be performed at a relatively slow rate, which relieves the need for additional supply voltage to allow for compensation during the output pulses.

Preferably, the output current is alternately compared against predetermined high and low control limits, and the output voltage is varied only if an exception condition is determined to exist, that is, a condition in which the output current falls outside these set limits. If desired, the adjustment may be made for multiple cycles of an exception condition. Alternatively, the measurements may be performed over a sequence of pulses by successive approximations of the output, and adjustments made accordingly.

Output current level varies during a "constant voltage" output pulse, and therefore a definition of the output current magnitude to be maintained must be established. For example, the output current magnitude may be defined as that at the leading edge, or the midpoint, or the trailing edge of the pulse; or as the mean current during the pulse. The trailing edge current magnitude is the preferred designation for control purposes, to reduce system complexity. A trailing edge measurement can be performed with a relatively slow sampling circuit (in contrast, for example, to the requirement for a leading edge measurement), and does not require the generation of special timing control signals which must vary with programmed pulse duration.

An alternative to the preferred technique of measuring the current magnitude at the trailing edge, on a pulse sampling basis, is to perform the measurement at the midpoint of the output pulse. This is a close approximation of the mean current level of the sampled pulse, with a requirement of only minimal additional energy overhead. The sampling in this case could be biased toward the second half of the pulse, to improve the approximation.

FIG. 1 is a simplified block diagram of an exemplary stimulus (pulse) generator of an excitable tissue stimulating device to which the principles of the present invention may be applied. Such a device, a neurostimulator for example, although the present invention is not limited to that application, may be implanted in or employed external to a patient's body to treat and/or control various disorders by application of modulating electrical signals to selected tissue such as a nerve of the patient. The location of an implanted device for stimulating the patient's vagus nerve, and details of the lead and electrode system of the device are illustrated in FIGS. 2A and 2B. A detailed description of a basic neurostimulator to which the principles of the present invention may be applied, apart from the modifications which will be described herein for implementing the invention, is contained in copending U.S. patent application Ser. No. 07/434,895, filed Nov. 10, 1989 in the names of Reese S. Terry, Jr., et al. (referred to herein as "the '895 application"), assigned to the same assignee as the instant application. The '895 application is incorporated herein by reference, but certain pertinent portions are summarized below for the sake of convenience to the reader.

The neurostimulator utilizes a conventional microprocessor among other standard electrical and electronic components, and in the case of an implanted device, communicates by asynchronous serial communication with a programmer and/or monitor located external to the patient's body for controlling or indicating states of the device. Passwords, handshakes and parity checks are employed for data integrity. Pulse generator 10 of the neurostimulator may be adapted for implantation in the patient in a pocket formed by the surgeon just below the skin in the chest as shown in FIG. 2A, or may be a primarily external system. The neurostimulator also includes an implantable stimulating electrode array 40 and electrical lead system 42 (FIGS. 2A and 2B) for applying the output signal of generator 10 to the selected nerve, such as the vagus nerve. Components external to the patient's body include a computer 53 and wand 55 for telemetry of parameter programming to and monitoring signals from generator 10 (or an associated sensing circuit). The programmed stimulating output pulse sequence of the pulse generator is delivered to the nerve(s) to modulate the electrical activity thereof.

In the device of FIG. 1, generator 10 includes a battery (for example, a single lithium thionyl chloride cell) 12 and voltage regulator 15 to supply a clean, steady output voltage to other components of the device, including a logic and control section 17. The latter includes a microprocessor to control programmable functions of the device including current, frequency, pulse width, on-time and off-time of the output signal. The output signal may thus be tailored to achieve the desired modulation of electrical activity of the nerve. Timing signals for the logic and control functions of the generator are provided by a crystal oscillator 20. A magnetically-actuated reed switch 27 is incorporated in the electronics package to provide the capability for manual activation of the generator (e.g., by the patient, using an external magnet, not shown, placed immediately adjacent to the generator implant site). Built-in antenna 25 enables communication between the implanted pulse generator and the external electronics via the wand 55. Once the system is programmed, it maintains and operates at the programmed settings until reprogrammed (by the attending physician).

Logic and control section 17 controls an output circuit 22 which generates the output signal having parameters programmed to enable treatment of the disorder of interest The output circuit and its programmed output signal are coupled to an electrical connector 30 on the housing 35 of generator 10 and, via the connector, to lead assembly 42 connected to the stimulating electrode array 40 (FIGS. 2A and 2B). Housing 35 is hermetically sealed and composed of a material such as titanium which is biologically compatible with the fluids and tissue of the patient's body. Further details of the structure and operation of the basic neurostimulator are set forth in the '895 application.

As shown in FIGS. 2A and 2B, nerve stimulating electrode array 40 is conductively connected to the distal end of insulated electrically conductive lead assembly 42 which is attached at its proximal end to connector 30 on the generator. Electrode array 40 may be a bipolar stimulating electrode of the type described in U.S. Pat. No. 4,573,481 to Bullara. In this example, the electrode array is surgically implanted on the vagus nerve 45 in the patient's neck. The two electrodes 43 and 44 are wrapped about the nerve, and the assembly is secured to the nerve by a spiral anchoring tether 47 of the type disclosed in U.S. Pat. No. 4,979,511 to Reese S. Terry, Jr., assigned to the same assignee as the instant application. Lead assembly 42 is secured in place by a suture connection 50 to nearby tissue, but can flex with movement of the patient's chest and neck.

Figure 3:
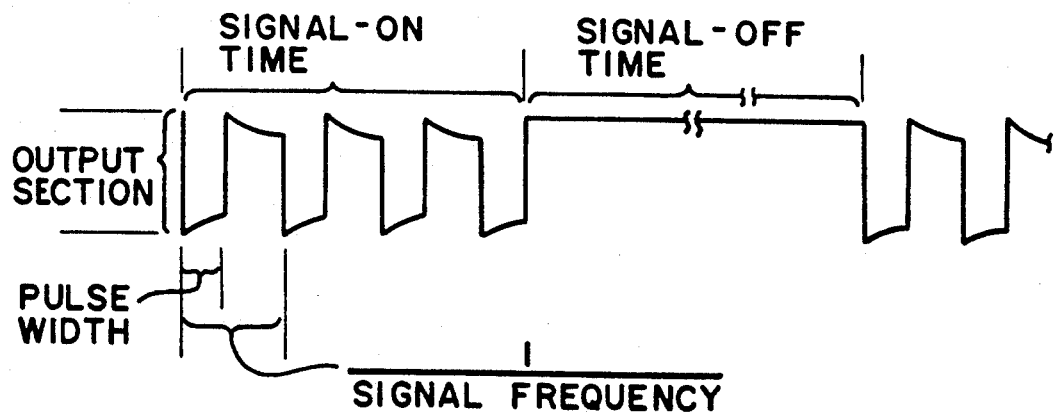
FIG. 3 is a simplified timing diagram of a typical output signal waveform of the neurostimulator of FIG. 1.

FIG. 3 is an idealized representation of an exemplary signal waveform which may be delivered by output circuit 22 of the neurostimulator pulse generator to electrode array 40, and is presented principally to clarify terminology, including signal-on time, signal-off time, signal frequency, pulse width, and output current.

A block diagram of a preferred embodiment of a control loop modification of output circuit 22 to implement the current stabilization mode of the invention is shown in FIG. 4. The control loop uses a digital control system which includes the microprocessor in logic/control section 17 to detect and measure the output signal of output circuit 22, and to supply a feedback signal for adjusting the current magnitude of the output pulses of the generator. Logic/control section 17 has several control and command function outputs from the microprocessor which are delivered variously to the output circuit and to the control loop 60. The output circuit includes a pair of switches (e.g., field effect transistors) 65, 67 which are actuated by command voltages from the microprocessor on paths 73 and 77, respectively. A signal voltage line 68 delivers the output pulses to the patient (via lead assembly 42 and electrode array 40), with the circuit completed through a return path 70 having a DC blocking capacitor 72 connected to the lead/electrode array.

When a pulse (or pulse sequence) is to be delivered to the nerve (i.e., signal-on time), switch 65 is turned on to deliver charge from storage capacitor 66 (according to the programmed pulse width and cycle/frequency) by commands on line 73 from the microprocessor. When switch 65 is on (and assuming a negative voltage on line 68 from the battery 12 or voltage regulator 15, and therefore on the storage capacitor 66), the output current flows from the capacitor through the ground path, through a low-valued (e.g., ten ohm) current sampling resistor 75, output path 70, blocking capacitor 72, the leads and nerve electrode, and back on path 68 to storage capacitor 66. When switch 65 is turned off, the voltage drops sharply to zero (from its higher negative value) with cessation of the pulse. The capacitor then recharges with the small amount of energy which was discharged, to the set output voltage level, in preparation for delivery of the next pulse.

With each pulse delivered to the nerve, there is an incremental build-up of charge on blocking capacitor 72 which, if left stored, could soon reach a level completely opposing the voltage delivered from the regulator and thereby rendering the output circuit ineffective. To prevent such an occurrence, the blocking capacitor is periodically discharged by turning switch 67 on with a command voltage from the microprocessor on line 77.

For purposes of stabilizing the output current, control loop circuit 60 periodically takes sample measurements of the output pulses, preferably at the trailing edge (or, alternatively, at the midpoint) of the pulse. The sampling is performed by a sample and hold circuit 80 which takes a reading of the current magnitude on line 81 from resistor 75, when actuated by a "sample current" command on line 84 from the microprocessor. To provide greater accuracy, the read value is boosted by the gain of an amplifier 85, which is calibrated based on a target (i.e., predetermined desired) current level from digital-to-analog (D/A) converter 86 supplied by a programmed digital value from the microprocessor on line 87.

The sample level is compared to the target level by comparator 88, which produces an output indicative of whether the sample level is greater or less than the target level, and the output information is fed back on line 90 to logic/control section 17. The output voltage level of the generated pulses is varied by an adjustment circuit 91 to reduce any discrepancy from the target current level. Adjustment circuit 91 is coupled to a programmable multiplier 92 in output circuit 22 (or other source of the final voltage level for the output pulses), which is nominally set by the microprocessor to multiply the battery voltage by any of a plurality of values (for example, 0.5, 1.0, 1.5, 2.0, 3.0) suitable to bring the output current level to the target level by corresponding adjustment of the output voltage of the pulses.

Adjustment circuit 91 includes a D/A converter 93 which receives a digital target voltage level on line 94 from the microprocessor 58, based on the results of the latest measurement performed by control loop circuit 00. This is compared, after conversion to an analog value, with the voltage level of the output from the programmable multiplier on line 68, in comparator 95. The output of the comparator on line 97 turns the multiplier on or off to produce the necessary adjustment according to the incremented setting of the multiplier by the microprocessor, to achieve the desired output current stabilization.

A charge stabilization mode of operation can achieve even greater energy savings than the current stabilization mode. Suitable embodiments and methods for implementing a charge stabilization mode for the output circuit of a tissue stimulating pulse generator according to the present invention will be described, by exemplary reference to nerve stimulation. It is known that the charge required to excite a cell membrane of excitable nerve tissue is relatively constant, within limits. At wide pulse widths, the charge required to be delivered increases as a result of decreased potential across the cell membrane. The decreased potential is attributable to accommodation processes related to cell membrane active transport of ions. Within a range of pulse durations in the temporal vicinity of the membrane time constant, the energy required for stimulation is minimized.

Compensation for the membrane time constant must be considered. For any excitable cell which has fully recovered . from previous stimulations. the voltage across its membrane which will cause regenerative depolarization is relatively constant over a wide range of pulse durations. For extremely short pulse widths (less than a few microseconds or tens of microseconds), however, this principle does not hold. Two competing factors determine the energy efficiency of stimulative pulses. For short duration pulses, resistive losses in the conducting medium reduce efficiency because the membrane behaves much as a capacitance. For a given voltage change across the membrane a fixed charge must be applied, and in the case of narrow pulses this is performed more rapidly by an inversely proportional increase in the delivered current. Although the current required to stimulate increases in inverse proportion to the output pulse duration, the energy loss in the surrounding medium varies as the square of the delivered current since energy is the time integral of the power. The power dissipated is equal to the resistance times the square of the current, assuming that the surrounding media are modeled as resistances, which is true of all but the pulse generator output capacitance and any electrode polarization.

If this were the only factor to be considered, then the wider the pulse the lower the energy required to stimulate, and a constant charge would be required at any pulse duration. When longer stimulating pulse durations are considered, the membrane model lust be modified to include a parallel conductance to account for leakage through the membrane, active transport mechanisms in the membrane, and leakages around the membrane. As each output pulse charges the membrane, some charge bleeds away. This is well modeled by an integrator with bleeder resistance, which may be used in the control loop to more efficiently control the output pulses to induce the threshold charge across the excitable tissue membranes.

In the charge stabilization mode of the present invention, the charge delivered in an output pulse is monitored by integrating the current in the output pulse as a measure of the charge. That information is then used to adjust the output pulse duration of the neurostimulator generator within a predetermined range of pulse widths. Whenever the pulse width is outside this range, a multiplier setting may be changed appropriately to maintain the desired output charge.

Capacitive multipliers and dividers may be utilized to produce different relatively low voltages with greater efficiency than by use of other methods. Voltage levels related to the system input voltage (i.e., a battery voltage for implantable devices) can be produced with maximum efficiency as a simple ratio of integers. Ratios such as 1/3, 1/2, 2/3, 3/2, 2/1, 3/1, and 4/1 are easily obtained. In practical devices, these settings are probably too coarse for constant current control, but use of charge stabilization control with pulse duration as the primary control variable allows these relatively widely spaced voltages to achieve the desired results.

An algorithm may be used to maintain constant output charge in the presence of changing impedances or changing battery voltage. In theory, if the supply voltage is adequate, output charge stabilization may be provided over a broad range of pulse durations. For maximum energy efficiency, however, only pulse durations which are in the temporal neighborhood of the membrane time constant of target cells are optimum. If the time constant of the output circuit is shorter than or sufficiently close to the membrane time constant, the range of optimal pulse widths is modified to be of shorter duration. In either event, the device design and target cells serve to determine an appropriate range of pulse widths. If the output control algorithm produces pulse durations at or beyond these limits, the output voltage should be changed in a direction to return the pulse duration toward the optimum.

A preferred method resolves either situation, i.e., in which the pulse duration is too long or too short. In the former case, the voltage multiplier setting is increased by one step and the output voltage is slowly ramped up. During this ramp up time, the control loop functions to ramp down the output pulse duration. Ramping is ceased when the output voltage reaches a point that is efficiently produced by the new multiplier setting. In the case where the output pulse duration is too short, the output voltage is slowly ramped down, which causes a gradual increase in the output pulse duration. When the output voltage reaches a level that is efficiently producible at the next lower voltage multiplier setting, that setting is used and the ramping is ceased.

Use of such a charge stabilization control algorithm avoids problems which may be encountered by other algorithms which cause the voltage to be changed because the computed pulse duration is not within the allowed range. For example, an algorithm that changes two variables simultaneously by relatively large amounts may result in significant changes in effectiveness of tissue stimulation. The preferred method for the charge stabilization mode allows the voltage to be increased or decreased in relatively small regulated steps (which themselves may be produced relatively inefficiently) toward the next efficiently produced capacitor multiplier ratio. These intermediate steps are not stable, and the algorithm continues to step the voltage in the direction of the stable points.

The pulse duration region at or near which it is no longer true that the charge required to stimulate a nerve cell membrane is relatively constant for durations significantly less than the membrane time constant, coincides with pulse durations for which stimulation is achieved with minimal energy. For a given membrane type these perturbations can be modeled from the ideal, and the model can then be used to make adjustments to the delivered pulse duration. One technique for accomplishing this is to modify the integrator which measures the delivered charge from the output current and time. As observed above, a bleeder resistance or current source may be added to the integrator to model the excitable cell's membrane ion pump activity. Maintaining the output of this system constant at the end of each output pulse, rather than simply maintaining the output charge constant on the same basis, serves to more accurately stabilize the tissue stimulation. The same goal may be achieved with a digital system. The curve relating threshold charge to pulse width is programmed into the control system, the measured charge is multiplied by the reciprocal of this curve, and the result is used as the regulated variable.

Figure 5A:
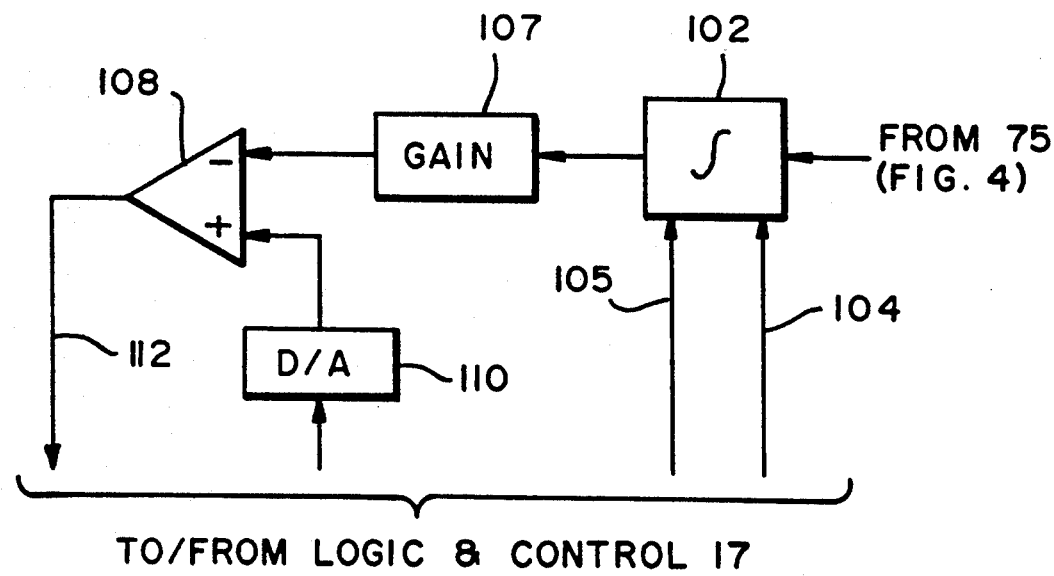
FIGS. 5A and 5B are block diagrams of alternative implementations of the charge stabilization mode of the invention, in the neurostimulator of FIG. 1.
Figure 5B:
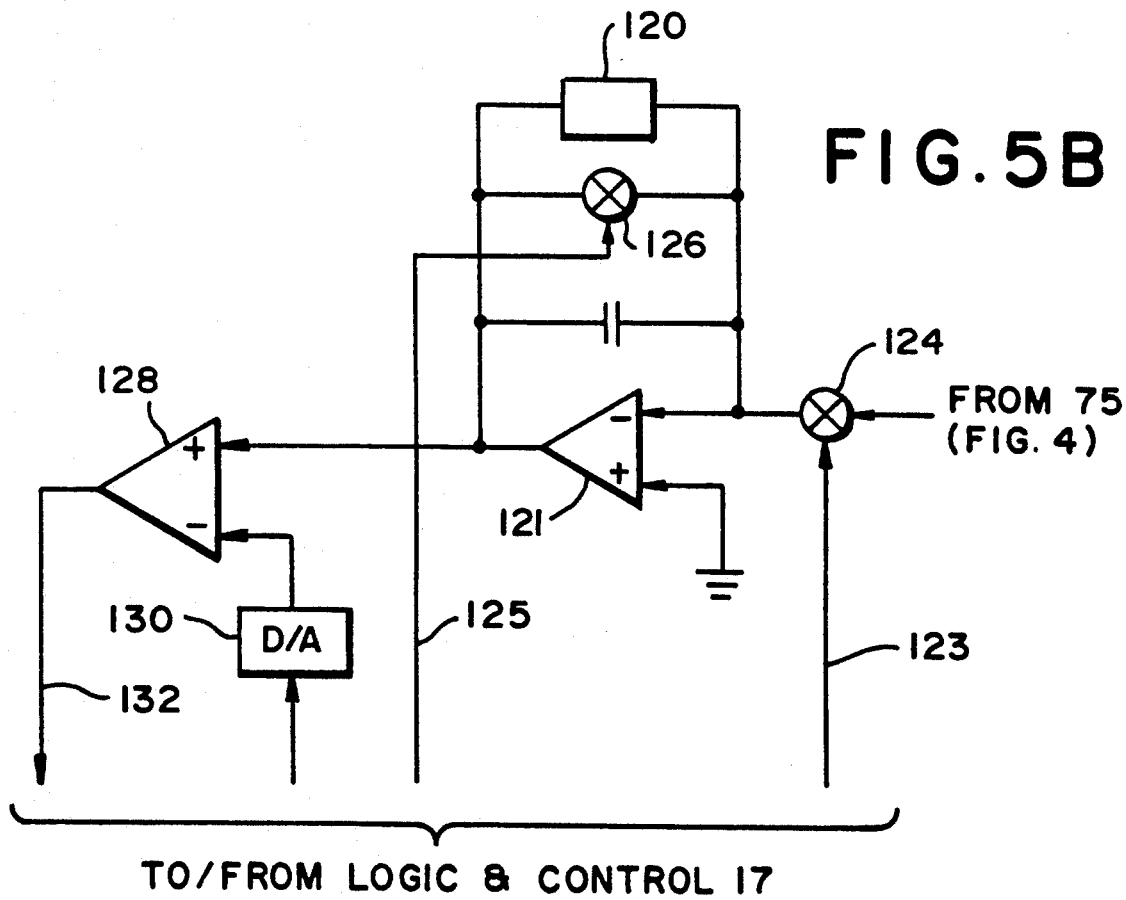

A pair of embodiments of a circuit for implementing the charge stabilization mode in conjunction with the output circuit 22 of neurostimulator generator 10 are shown in block diagrammatic form in FIGS. 5A and 5B. In both embodiments, the circuitry employed is substantially the same as that utilized for the current stabilization mode embodiment of FIG. 4, except for the control loop portion 60, with adjustment of output pulse duration. Accordingly, the description of the two charge stabilization mode embodiments will be substantially limited to a description of the modified control loop portion.

In the first implementation of the charge stabilization mode circuit, partially shown in FIG. 5A, the current taken from the sampling resistance 75 is applied to a integrator 102 controlled by the microprocessor in logic/control section 17 to perform an integration of pulse current over the output pulse duration time interval and to hold the results of the integration, in response to appropriate command inputs on line 104. The output of the integrator therefore represents the charge delivered in the respective output pulse sample. At the end of each sample interval, the integrator 102 is reset by a command from the microprocessor on line 105, in readiness for integration of the next sample.

The output level of the integrator is boosted in an amplifier 107 and applied to one input of a comparator 108. The other input to the comparator is from a D/A converter 110 which provides an analog value of a target charge level from the digital value thereof inputted from the microprocessor. Any discrepancy between the two values under comparison is reflected at the output 112 of the comparator, and is utilized to adjust the duration of the output pulses to stabilize the charge delivered in the output pulses. If too little charge has been delivered, the pulse durations are increased; if too much charge is delivered, the pulse durations are decreased.

In the alternative implementation of the charge stabilization mode portion shown in FIG. 5B, a similar operation is performed to that of FIG. 5A except that provision is made for membrane loss modelling as generally described above. The integrator which derives a measure of the charge delivered in a sampled pulse by integrating the pulse current over a preset time is modified by using a resistance or current source 120 to model the cell membrane repolarization for excitation. In essence, the bleeder resistance or current source 120 across amplifier 121 models the situation in which the charge is being bled off as the output pulse is seeking to charge the cell membrane. The amplifier circuit acts like an integrator in summing its inputs over time. Commands 123 and 125 from the microprocessor activate switches 124 and 126 respectively. A comparator 128 receives inputs from the modelled cell membrane repolarization and from a D/A converter 130 provides the target charge level from the microprocessor. Here again, the discrepancy from the comparison at output 132 is used to adjust the duration of the output pulses to stabilize the charge delivered in the output pulses. The control loop circuit operates to maintain the membrane charge constant (at a programmed value) at the end of each output pulse, which has the effect of stabilizing the tissue stimulation.

It will be seen from the foregoing description that output stabilization systems constructed according to the principles of the present invention provide superior energy conservation in either the current stabilization mode or the charge stabilization mode, without sacrificing system performance and, indeed, while improving operating efficiency.

Although certain presently preferred embodiments and methods of making such embodiments of the invention have been described herein, it will be apparent to those skilled in the relevant field to which the invention pertains from a consideration of the foregoing description, that variations and modifications of the disclosed embodiments and methods may be made without departing from the spirit and scope of the invention. It is therefore intended that the invention shall be limited only to the extent required by the appended claims and the rules and principles of applicable law.

What is claimed is:

1. An implantable tissue stimulator for delivering stimulating pulses to selected tissue of a patient via one or more electrodes implanted on or near the tissue, comprising:

pulse generator means for sequentially generating output pulses in a programmable pattern for application to the tissue, and control loop means connected to the pulse generator means for measuring the magnitude of a predetermined parameter of selected ones of the output pulses at a predetermined point of the selected pulses and for adjustment of said magnitude to stabilize the value thereof for subsequent ones of the output pulses, the control loop means including adjustment means responsive to measurements of said magnitude differing from a predetermined value for controlling the pulse generator means to adjust said predetermined parameter of the output pulses to reduce the difference to within a preselected amount.

2. The invention of claim 1, wherein the control loop means includes measurement means for measuring said magnitude periodically.

3. The invention of claim 2, wherein the measurement means measures said magnitude over separated cycles of the output pulses.

4. The invention of claim 1, wherein said predetermined parameter is current delivered in each output pulse, and the control loop means includes measurement means for performing said measurements, the measurement means including means for performing successive approximations of the magnitude of the current of said selected ones of the output pulses by measuring the current magnitude of at least one output pulse but not all output pulses per burst and completing the approximation after a sequence of bursts.

5. The invention of claim 1, wherein
said predetermined parameter is current, and
the control loop means includes measurement means for performing said periodic measurements, the measurement means . including:
  limit means for establishing predetermined high and low control limits for the current magnitude of the output pulses, and
  comparison means for alternately comparing the current magnitude of selected ones of the output pulses against the established high and low control limits, and
the adjustment means includes:
  varying means responsive to the comparison means for varying the voltage of the output pulses to bring the current magnitude of the pulses within said limits when the comparison means determines that either limit is exceeded.

6. The invention of claim 5, wherein the varying means is responsive to the comparison means to vary said current magnitude to fall within said limits only when the comparison means determines that multiple ones of the output pulses in each sequence have exceeded at least one of said limits.

7. The invention of claim 1, wherein said predetermined parameter is current, and said predetermined point of the selected pulses at which the measurement is performed is the trailing edge of the respective selected pulses.

8. The invention of claim 1, wherein
said predetermined parameter is current, and
said predetermined point of the selected pulses at which the measurement is performed is the approximate midpoint of the respective selected pulses.

9. The invention of claim 1, wherein said measurements are performed by sampling the output pulses at a rate much less than the frequency at which the output pulses are generated.

10. The invention of claim 1, wherein
said predetermined parameter is charge delivered in the output pulse, and
said adjustment means is responsive to measurement of charge in an output pulse differing from said predetermined value for controlling the pulse generator means to adjust the duration of the output pulses to reduce the difference to within a preselected amount.

11. The invention of claim 1, wherein
said predetermined parameter is charge delivered in the output pulse, and
the control loop means including measurement means for performing said measurements, the measurement means including:
  limit means for establishing predetermined high and low control limits for the charge magnitude of the output pulses, and
  comparison means for comparing the charge magnitude of said selected ones of the output pulses against said high and low control limits, and
the adjustment means includes:
  means responsive to the comparison means for varying the duration of the output pulses to bring the charge magnitude of the pulses within said limits when the comparison means determines that either of said limits is exceeded.

12. The invention of claim 1, wherein
said predetermined parameter is charge delivered in the output pulse, and
the control loop means includes measurement means for performing said measurements, the measurement means including:
  means for integrating the output pulse current over a predetermined time interval to determine the magnitude of the charge delivered in each output pulse.

13. The invention of claim 1, wherein
said predetermined parameter is charge delivered in the output pulse, and
the control loop means further includes means for modelling the excitable cell membrane repolarization of the selected tissue to control the output pulse durations to induce a threshold charge across the membrane sufficient for excitation thereof.

14. The invention of claim 1, wherein
said predetermined parameter is charge delivered in the output pulse, and
the control loop means further includes means for modelling the charge delivered in each output pulse to induce a threshold charge across the excitable cell membranes of the tissue to be stimulated which accounts for charge loss attributable to leakage from the membranes.

15. Apparatus for stabilizing the value of the amount of electrical charge delivered in each of the output pulses of a neurostimulator for stimulating the excitable cell membranes of a selected nerve, comprising:
  measuring means for ascertaining the value of said electrical charge of the output pulses,
  comparing means responsive to the ascertained value for comparison thereof with a target value reflecting a desired limit on the value of said electrical charge, and
  adjusting means responsive to a discrepancy between the values under comparison for adjusting the duration of each output pulse to reduce the discrepancy and thereby stabilize the value of the electrical charge, whereby to control the output pulses of the neurostimulator to enhance the efficiency of stimulation of the nerve membranes, said adjusting means including means for immediately ending a pulse when the target value is reached.

16. Apparatus for stabilizing the value of a parameter of the output pulses of a neurostimulator for stimulating the excitable cell membranes of a selected nerve, comprising:
  measuring means for sampling the value of said first parameter of the output pulses intermittently at separated cycles of the output pulses to ascertain the value of said parameter,
  comparing means responsive to the ascertained value of said parameter for comparison thereof with a target value reflecting a desired limit on the value of said parameter, and adjusting means responsive to a discrepancy between the values under comparison for adjusting the value of a second parameter of the output pulses related to the first-mentioned parameter to reduce the discrepancy and thereby stabilize the value of the first parameter, whereby to control the output pulses of the neurostimulator to enhance the efficiency of stimulation of the nerve membranes.

17. The invention of claim 16, wherein said comparing means compares the sampled value of the first parameter against a pair of upper and lower target values representing limits on the value of the first parameter.

18. The invention of claim 17, wherein the measuring means samples the value of the first parameter at a rate much slower than the rate at which the output pulses are generated.

19. The invention of claim 18, wherein said adjusting means adjusts the value of the second parameter to reduce the discrepancy only when the sampled value is outside desired upper and lower limits reflected by said pair of target values.

20. The invention of claim 18, wherein the adjusting means adjusts the value of the second parameter to reduce the discrepancy only when the sampled value is outside desired upper and lower limits reflected by said pair of target values over a multiplicity of pulse cycles.

21. The invention of claim 16, wherein the first parameter is the output pulse current.

22. The invention of claim 21, wherein the second parameter is the output pulse voltage.

23. The invention of claim 1, wherein the first parameter is the amount of electrical charge delivered in each output pulse.

24. The invention of claim 23 wherein the second parameter is the output pulse voltage.

25. The invention of claim 23, wherein the second parameter is the output pulse duration.

26. Apparatus for stabilizing the value of a parameter of the output pulses of a neurostimulator for stimulating the excitable cell membranes of a selected nerve, comprising:
    measuring means for ascertaining the value of said parameter of the output pulses by performing a series of successive approximations of said parameter over a sequence of said output pulses,
    comparing means responsive to the ascertained value of said parameter for comparison thereof with a target value reflecting a desired limit on the value of said parameter, and
    adjusting means responsive to a discrepancy between the values under comparison for adjusting the value of a second parameter of the output pulses related to the first-mentioned parameter to reduce the discrepancy and thereby stabilize the value of the first parameter, whereby to control the output pulses of the neurostimulator to enhance the efficiency of stimulation of the nerve membranes.

27. A method of stimulating body tissue, which comprises:
    implanting a stimulating electrode adjacent the tissue to be stimulated;
    applying electrical pulses to the electrode to stimulate the tissue; and
    continually adjusting the level of current or charge delivered in the applied electrical pulses to maintain the value thereof within a predetermined range of values deemed most efficient for exciting the tissue to be stimulated, including adjusting the voltage level or the duration of the output pulses, and further including modelling the charge delivered in each output pulse to be constant for compensation thereof according to the time constant of the excitable cell membranes of the tissue to be stimulated.

28. The method according to claim 27, wherein the continual adjustment of the level of current or charge delivered in the output pulses further includes automatically terminating each output pulse upon delivery of an electrical charge therein which is sufficient to excite the cell membranes of the tissue, whether such charge is compensated or not.

29. A method of stimulating body tissue, which comprises:
    implanting a stimulating electrode adjacent the tissue to be stimulated;
    applying electrical pulses to the electrode to stimulate the tissue; and
    continually adjusting the level of current or charge delivered in the applied electrical pulses to maintain the value thereof within a predetermined range of values deemed most efficient for exciting the tissue to be stimulated, including adjusting the voltage level or the duration of the output pulses, and further including modelling the charge delivered in each output pulse to induce a threshold charge across the excitable cell membranes of the tissue to be stimulated which accounts for charge loss attributable to leakage from the membranes.

30. Apparatus for stabilizing the magnitude of the current of the output pulses of a neurostimulator for stimulating the excitable cell membranes of a selected nerve, comprising:
    measuring means for measuring the magnitude of the current of selected ones of the output pulses by sampling the current magnitude at a predetermined point of the selected pulses,
    comparing means responsive to the measured value of the current magnitude for comparison thereof with a target value reflecting a desired limit on the current magnitude, and
    adjusting means responsive to a discrepancy between the values under comparison for adjusting the value of a second parameter of the output pulses related to current magnitude thereof to reduce the discrepancy and thereby stabilize the value of the current magnitude, whereby to control the output pulses of the neurostimulator to enhance the efficiency of stimulation of the nerve membranes.

31. The invention of claim 30, wherein the measuring means performs the sampling at the trailing edge of the output pulses in separated cycles thereof.

32. The invention of claim 30, wherein the measuring means performs the sampling near the midpoint of the output pulses in separated cycles thereof.

* * * * *